United States Patent [19]

Badylak et al.

[11] Patent Number: 5,275,826
[45] Date of Patent: Jan. 4, 1994

[54] FLUIDIZED INTESTINAL SUBMUCOSA AND ITS USE AS AN INJECTABLE TISSUE GRAFT

[76] Inventors: Stephen F. Badylak, 2610 Nottingham Pla., West Lafayette, Ind. 47906; Robert J. Demeter, 360 Cottonwood Dr., Mooresville, Ind. 46158; Michael Hiles, 3817 Cologne Ct., Indianapolis, Ind. 46208; Sherry Voytik, 271 S. River Rd., Apt. #33, West Lafayette, Ind. 47906; Peter M. Knapp, Jr., 1009 Laurelwood, Carmel, Ind. 46032

[21] Appl. No.: 976,156
[22] Filed: Nov. 13, 1992
[51] Int. Cl.$^5$ ............................................. A61K 35/38
[52] U.S. Cl. ..................................... 424/551; 623/14
[58] Field of Search ......................... 424/551; 623/14
[56] References Cited

U.S. PATENT DOCUMENTS 4,902,508  2/1990  Badylak et al. ..................... 424/551
4,956,178  9/1990  Badylak et al. ..................... 424/551

OTHER PUBLICATIONS

"Polytef Augmentation Urethroplasty", Solomon Berg. *Arch. Surg.* vol. 107, Sep. 1973, pp. 379-381.
"Teflon Injection in Stress Incontinence", A. M. Deane, et al., *British Journal of Urology*, (1985), 57, 78-80.
"Periurethral Teflon Injection: A Simple Treatment for Urinary Incontinence", K. B. Lim, et al, *British Journal of Urology*, (1983), 55, 208-210.
"Periurethal Teflon Injection For Urinary Incontinence", Victor A. Politano, et al., *The Journal of Urology*, Feb. 1974, pp. 180-183.
"Treatment of Urinary Incontinence by the Periurethral Implantation of Glutaraldehyde Cross-Linked Collagen", Linda M. D. Shortliffe, et al., *The Journal of Urology*, vol. 141, Mar. 1989, pp. 538-541.
"Why We've Abandoned Polytef Injection for VUR", Mark. Burns et al., *Contemporary Urology*, Dec. 1991, pp. 40-43.
"Replacement of Dog's Aorta by Autologous Intestinal Muscle in the Infected Retroperitoneum", R. Broll, et al., *Eurp. Surg. Res.*, 18:390-396 (1986).
"Comparison of Bovine Collagen Xenografts to Autografts in the Rabbit", J. C. Tauro, et al., *Clinical Orthopaedics and Related Research*, No. 266, May, 1991, pp. 271-284.
"Development of a Reconstituted Collagen Tendon Prosthesis", Jack D. Goldstein, et al., *The Journal of Bone and Joint Surgery, Incorporated*, vol. 71-A, No. 8, Sep. 1989, pp. 1183-1191.
"Aortic Replacement with Multi-Layer Submucosa Prostheses Made From Heterologous Small Intestine", G. Rotthoff, et al., presented at 8th Congress of the International Society of Cardiovascular Surgery, Vienna, Sep. 7-9, 1967.
"Replacement of the Abdominal Aorta by an Ileum Muscle Tube in an Animal Experiment", J. Huth, et al., (translation), *Thoraxchir. Vask, Chir.*, 15(4): 401-407, Aug. 1967.
"Long Term Observations and Histological Studies on Vessel and Heart Wall Grafts From Small Intestine", R. Haring, et al., *Langenbecks Arch. Klin. Chir.*, 1965, 313:664-8.
"Replacement of the Abdominal Aorta With a Small-Intestine Muscle Tube In An Animal Experiment", J. Huth, *Zentralbl Chir.*, 92 (26/2): 1817-19 (1967).
"Reconstruction of the Arterial Flow Path by Autologous Intestinal Muscle Grafts in the Dog", H. P. Bruch, et al., *Folia Angiologica*, vol. 29 (3-5/81) pp. 65-68.
"Replacement of the Aorta by Multilayered Submucosa Prostheses of Heterologous Ileum", G. Rotthoff, et al., *Bulletin de la Societe International de Chirurgie*, No. 2, 1969, 256-259.

*Primary Examiner*—Douglas W. Robinson
*Assistant Examiner*—Jean C. Witz
*Attorney, Agent, or Firm*—Barnes & Thornburg

[57] ABSTRACT

A fluidized, injectable tissue graft composition is described. The composition comprises comminuted intestinal submucosa or protease-digested intestinal submucosa. Methods for the preparation and use of injectable tissue graft compositions are described. In preferred embodiments the tissue graft material is prepared from the intestinal submucosa comprising the tunica submucosa, the muscularis mucosa and the stratum compactum of a segment of intestinal tissue of a warm-blooded vertebrate. Effective amounts of the fluidized graft compositions can be injected to promote repair tissue defects by inducing formation of endogenous tissues.

26 Claims, No Drawings

FLUIDIZED INTESTINAL SUBMUCOSA AND ITS USE AS AN INJECTABLE TISSUE GRAFT

BACKGROUND AND SUMMARY OF THE INVENTION

The present invention relates to an injectable tissue graft composition and methods for its preparation and use. More particularly, the present invention is directed to injectable, non-immunogenic tissue graft compositions derived from intestinal submucosa. Upon deposition in vivo in an area of a tissue defect, the present fluidized tissue graft compositions promote growth of endogenous tissue to repair the defect.

It has been reported that compositions comprising the submucosa and the basilar portions of the tunica mucosa of the intestine of warm-blooded vertebrates can be used as tissue graft materials in sheet form. See U.S. Pat. No. 4,902,508. The preferred trilaminate sheet compositions described and claimed in that patent are characterized by excellent mechanical properties, including high compliance, a high burst pressure point, and an effective porosity index which allowed such compositions to be used beneficially for vascular graft constructs. The graft materials disclosed in that patent are also useful in tendon and ligament replacement applications. When used in such applications the preferred trilaminate graft constructs appear to serve as a matrix for the regrowth of the tissues replaced by the graft constructs. It was believed that such properties derived from the unique trilaminate sheet structures of the intestinal tissue derived graft constructs.

Surprisingly, it has been discovered that intestinal submucosa can be fluidized by comminuting and/or protease digestion, without loss of its apparent biotropic properties, for use in less invasive methods of administration (e.g., injection or topical) to host tissues in need of repair.

According to the present invention, an injectable, non-immunogenic tissue graft composition is provided. In one embodiment the composition comprises comminuted large or small intestinal submucosa, preferably in an aqueous suspension. In another aspect of the invention, there is provided a composition comprising protease-digested intestinal submucosa.

The fluidized composition is used advantageously in a method for inducing formation of endogenous tissue including bone and soft tissues such as muscle and connective tissues in a warm-blooded vertebrate. The method comprises the step of injecting into the vertebrate a composition comprising a suspension of comminuted intestinal submucosa or a protease digest thereof in an amount effective to induce endogenous tissue growth in the locale of the injected fluidized tissue graft composition. Endogenous connective tissues induced to grow in accordance with this invention include collagen, elastin and muscle.

In another more specific aspect of the present invention, a method is provided for augmenting sphincter function in a warm-blooded mammal, the method comprising the step of injecting into tissue forming said sphincter an effective amount of a tissue graft composition comprising an aqueous suspension of comminuted intestinal submucosa. In yet a further aspect of the present invention, a method is provided for augmenting sphincter function in which the injectable composition comprises protease digested intestinal submucosa.

The injectable or "fluidized" compositions in accordance with the present invention can be used in a wide variety of tissue repair or tissue reconstruction applications. They can be used alone or in combination with the graft material described in U.S. Pat. No. 4,902,308.

For example, the compositions of the present invention can be used for surgical reconstruction of a collagenous meniscus at the interface of articulating bones. In such reconstruction a sheet of a first tissue graft composition, preferably itself comprising intestinal submucosa of a warm-blooded vertebrate, is formed into a sealed pouch and filled with a fluidized tissue graft composition of this invention.

Additional objects, features, and advantages of the invention will become apparent to those skilled in the art upon consideration of the following detailed description of preferred embodiments exemplifying the best mode of carrying out the invention as presently perceived.

DETAILED DESCRIPTION OF THE PREFERRED EMBODIMENTS

One preferred starting material for the compositions in accordance with the present invention comprises the tunica submucosa along with basilar portions of the tunica mucosa of a segment of intestinal tissue of a warm-blooded vertebrate. In particular, the preferred starting material comprises the tunica submucosa along with the lamina muscularis mucosa and the stratum compactum of a segment of small intestine, said layers being delaminated from the tunica muscularis and the luminal portion of the tunica mucosa of said segment. Such a material is referred to herein as Small Intestine Submucosa ("SIS") or "SIS trilaminate."

The preparation of SIS from a segment of small intestine is detailed in U.S. Pat. No. 4,902,508, the disclosure of which is expressly incorporated herein by reference. A segment of intestine is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use as described below.

The present fluidized compositions are prepared as solutions or suspensions of intestinal submucosa by comminuting and/or digesting the submucosa with a protease, such as trypsin or pepsin, for a period of time sufficient to solubilize said tissue and form a substantially homogeneous solution. The intestinal submucosa starting material is comminuted by tearing, cutting, grinding, shearing and the like. Grinding the submucosa in a frozen or freeze-dried state is preferred although good results can be obtained as well by subjecting a suspension of pieces of the submucosa to treatment in a high speed (high shear) blender and dewatering, if necessary, by centrifuging and decanting excess water. The comminuted intestinal submucosa can be dried to form a submucosa powder. Thereafter, it can be hydrated, that is, combined with water or buffered saline and optionally other pharmaceutically acceptable excipients to form a tissue graft composition as a fluid having a viscosity of about 2 to about 300,000 cps at 25° C. The higher viscosity graft compositions can have a gel or paste consistency. The present compositions can be sterilized using art-recognized sterilization techniques such as exposure to ionizing radiation.

The fluidized intestinal submucosa compositions of this invention can be used for the production of antibodies to the tissue graft material described in U.S. Pat. No. 4,902,508 using art-recognized hybridoma technology. The fluidized submucosa derived from SIS is injected into an immunologically competent animal to evoke the production of antibody-producing lymphocytes in the animal's spleen. The lymphocytes are fused with myeloma cells to form hybrid cells (hybridomas) which are screened for submucosa-antibody production. The monoclonal antibodies produced by culturing the selected hybridomas are isolated and used for detecting submucosal tissue in vivo and in vitro.

The fluidized submucosa of this invention also finds use as an injectable heterograft for tissues, for example, bone or soft tissues, in need of repair or augmentation most typically to correct trauma or disease-induced tissue defects. The present fluidized submucosa compositions are also used advantageously as a filler for implant constructs comprising, for example, one or more sheets of SIS formed into sealed (sutured) pouches or "pillows" for use in cosmetic or trauma-treating surgical procedures.

EXAMPLE 1

SIS Suspension

SIS specimens prepared as described above are minced or chopped into arbitrarily small pieces using tissue scissors, a single-edged razor blade, or other appropriate cutting implement. The specimens are placed in a flat bottom stainless steel container and liquid nitrogen is introduced into the container to freeze the specimens to prepare them for comminuting.

The frozen SIS specimens are then comminuted to form a coarse SIS powder. Such processing can be carried out, for example, with a manual arbor press with a cylindrical brass ingot placed on top of the frozen specimens. The ingot serves as an interface between the specimens and the arbor of the press. It is typically necessary to add liquid nitrogen periodically to the SIS specimens to keep them frozen.

Other methods for comminuting SIS specimens may be utilized to produce an SIS powder usable in accordance with the present invention. For example, SIS specimens can be freeze-dried and then ground using a manual arbor press or other grinding means. Alternatively, SIS can be processed in a high shear blender to produce, upon dewatering and drying, an SIS powder.

Further grinding of the SIS powder using a pre-chilled mortar and pestle can be used to produce consistent, more finely divided product. Again, liquid nitrogen is used as needed to maintain solid frozen particles during final grinding. The powder can be easily hydrated using, for example, buffered saline to produce a fluidized tissue graft material of this invention at the desired viscosity.

EXAMPLE 2

PIS Solution

SIS powder is sifted through a wire mesh into any convenient vessel. The powder is then subjected to proteolytic digestion to form a substantially homogeneous solution. In one embodiment, the powder is digested with 1 mg/ml of pepsin (Sigma Chemical Co., St. Louis, Mo.) in 0.1 M acetic acid, adjusted to pH 2.5 with HCl, over a 48 hour period at room temperature. The reaction medium is neutralized with sodium hydroxide to inactivate the peptic activity. The solubilized submucosa may then be concentrated by salt precipitation of the solution and separated for further purification and/or freeze drying to form a protease solubilized intestinal submucosa in powder form.

The viscosity of fluidized submucosa compositions in accordance with this invention can be manipulated by controlling the concentration of the submucosa component and the degree of hydration. The viscosity can be adjusted to a range of about 2 to about 300,000 cps at 25° C. Low viscosity submucosa compositions are better adapted for intraarticular applications or applications within body cavities. Higher viscosity formulations, for example, gels, can be prepared from the SIS digest solutions by adjusting the pH of such solutions to about 6.0 to about 7.0. Gel forms of the present compositions, as submucosa suspensions or submucosa digest solutions, are typically preferred for subcutaneous or intramuscular applications using syringes or catheters.

EXAMPLE 3

Applications

A. SIS as a suspension was utilized as a meniscus in five dogs. Specifically, the medial meniscus of normal crossbred adult dogs was removed and then replaced by a newly constructed SIS meniscus. This SIS meniscus consisted of a sheet of SIS (with stratum compactum "inside") formed into a semicircular pillow. The pillow was then filled with a suspension of SIS and the suture line of the pillow was attached to the medial collateral ligament. Thus, the substance of the pillow served as the weight bearing shock absorber between the medial femoral condyle and the tibial plateau. Three of the animals have been sacrificed. The first animal was sacrificed four months and four days after surgery. The second animal was sacrificed three months and twenty-one days after surgery and the fourth animal was sacrificed four months and three days after surgery. The results for all three animals were similar. The SIS/meniscus had formed a partially organized fibrocartilage material indistinguishable by histologic methods from the fibrocartilage of the normal meniscus. The shape of this newly formed meniscus was unlike a normal meniscus but the purpose of the study was simply to see whether connective tissue remodeling would occur and whether or not there would be any adverse reaction. There was absolutely no evidence of rejection, inflammation, or infection. Animals three and five are still living. In the above studies, pig SIS was used in the dog host.

B. SIS solution was injected in the subcutaneous site in four separate locations on the dog. In addition, the solution (pH=8.0) was injected in submucosal location of the vaginal wall and into the medial collateral ligament area of the knee. There was no evidence of rejection, infection, or abnormal physiologic response of the host animal. There is thickening of the injection sites. Control sites where saline was used as the injection material showed complete resorption of the material with no evidence of connective tissue thickening.

C. SIS suspension has been used to augment the urethral sphincter in three separate pigs. The suspension of SIS material was injected via endoscopy and via laparoscopy into the submucosal and subserosal locations of the pig urinary bladder. In addition, injections of the material (approximately 4 ml) have been injected in the submucosal location around the ureteral orifice bilaterally, and in the urinary bladder wall. One pig was sacrificed nine weeks after the initial injection and showed connective tissue remodeling with an infiltration of warm spindle shaped myofibroblasts which are positive for smooth muscle action. This type of connective tissue response is very similar to that seen-in the use of SIS tubes in the arterial location. Control sites where saline was used as the injection material showed no response. It was concluded that SIS stimulates an appropriate connective tissue remodeling such that augmentation of urinary bladder wall and/or urinary bladder sphincter can be accomplished with suspended SIS material.

The fluidized submucosa compositions of this invention find wide application both in tissue replacement and repair. The fluidized submucosal compositions are used in accordance with the present method to induce regrowth of natural connective tissue or bone in an area of an existent defect. By injecting an effective amount of a fluidized submucosa composition into the locale of a tissue defect or a wound in need of healing, one can readily take advantage of the graft compositions biotropic properties without the need for more invasive surgical techniques.

Perhaps the most remarkable aspect of the compositions of the present invention is their ability to induce regrowth of natural tissue in an affected area. By injecting an effective amount of a fluidized submucosa composition into the locale of a tissue defect or a wound in need of healing, one can readily take advantage of this surprising property without the need for major invasive operations.

Although the invention has been described in detail with reference to certain preferred embodiments, variations and modifications exist within the scope and spirit of the invention as described and defined in the following claims.

We claim:

1. A method of preparing an injectable tissue graft composition, said method comprising the steps of comminuting intestinal tissue consisting essentially of the tunica submucosa, the muscularis mucosa and stratum compactum of the tunica mucosa of the intestine of a warm-blooded vertebrate and hydrating the resultant comminuted intestinal tissue to provide said tissue graft composition as a fluid having a viscosity of about 2 to about 300,000 cps at 25° C.

2. The method of claim 1, wherein the comminuting step includes the step of freezing the intestinal tissue and grinding the frozen intestinal tissue.

3. The method of claim 1 wherein the comminuting step includes the steps of freeze-drying the intestinal tissue and grinding the freeze-dried intestinal tissue.

4. The method of claim 1 wherein the comminuting step includes the step of processing the intestinal tissue in a high shear blender.

5. The method of claim 1 further comprising the step of sterilizing the tissue graft composition.

6. The method of claim 1 further comprising the step of digesting the comminuted intestinal tissue with a protease for a period of time sufficient to solubilize said tissue to provide the tissue graft composition as a substantially homogeneous solution.

7. The method of claim 6, further comprising the step of neutralizing the substantially homogeneous solution to inactivate the protease.

8. The method of claim 6, further comprising the step of isolating the solubilized tissue from the substantially homogeneous solution.

9. A method of preparing an injectable tissue graft composition, said method comprising the step of digesting intestinal tissue consisting essentially of the tunica submucosa, the muscularis mucosa and stratum compactum of the tunica mucosa of the intestine of a warm-blooded vertebrate in aqueous solution with a protease for a period of time sufficient to solubilize said intestinal tissue to form a substantially homogeneous solution.

10. The method of claim 9, further comprising the step of neutralizing the substantially homogeneous solution to inactivate the protease.

11. The method of claim 9, further comprising the step of isolating the solubilized tissue from the substantially homogeneous solution.

12. An injectable, non-immunogenic tissue graft composition comprising a suspension of comminuted intestinal tissue consisting essentially of the tunica submucosa, the muscularis mucosa and stratum compactum of the tunica mucosa of the intestine of a warm-blooded vertebrate in an aqueous carrier.

13. The composition of claim 12 having a viscosity of about 2 to about 300,000 cps at 25° C.

14. An injectable, non-immunogenic tissue graft composition comprising a suspension of protease-digested intestinal tissue consisting essentially of the tunica submucosa, the muscularis mucosa and stratum compactum of the tunica mucosa of the intestine of a warm-blooded vertebrate in an aqueous carrier.

15. The composition of claim 14 having a viscosity of about 2 to about 300,000 cps at 25° C.

16. The composition of claim 14, wherein the composition is substantially free of protease.

17. A method of promoting wound healing in a patient in need thereof comprising the step of applying to a wound an effective amount of the injectable tissue graft composition of claim 12.

18. The injectable tissue graft composition of claim 12, dried and in powder form.

19. The injectable tissue graft composition of claim 14, dried and in powder form.

20. A method for inducing the formation of endogenous connective tissue in a warm-blooded vertebrate in need thereof comprising administering an effective amount of the tissue graft composition of claim 12 in an amount effective to induce endogenous tissue growth at the site the composition is administered.

21. The method of claim 20 wherein the growth induced endogenous tissue is bone or connective tissue comprising collagen, elastin or muscle.

22. The method of claim 20 wherein the tissue graft composition is injected into tissue forming a sphincter in a warm-blooded mammal and the growth induced tissue is tissue forming the sphincter.

23. A method for augmenting sphincter function in a mammal in need thereof comprising the step of injecting an effective amount of the tissue graft composition of claim 12 into tissue forming said sphincter.

24. A method of promoting wound healing in a patient in need thereof comprising the step of applying to a wound an effective amount of the injectable tissue graft composition of claim 14.

25. A method for inducing the formation of endogenous connective tissue in a warm-blooded vertebrate in need thereof comprising administering an effective amount of the tissue graft composition of claim 14 in an amount effective to induce endogenous tissue growth at the site the composition is administered.

26. A method for augmenting sphincter function in a mammal in need thereof comprising the step of injecting an effective amount of the tissue graft composition of claim 14 into tissue forming said sphincter.

* * * * *